(12) United States Patent
Dershem et al.

(10) Patent No.: US 6,423,780 B1
(45) Date of Patent: Jul. 23, 2002

(54) HETEROBIFUNCTIONAL MONOMERS AND USES THEREFOR

(75) Inventors: Stephen M. Dershem, San Diego; Kevin J. Forrestal, Poway, both of CA (US)

(73) Assignee: Loctite, Rocky Hill, CT (US)

( * ) Notice: Subject to any disclaimer, the term of this patent is extended or adjusted under 35 U.S.C. 154(b) by 0 days.

(21) Appl. No.: 09/779,396

(22) Filed: Feb. 7, 2001

(51) Int. Cl.$^7$ .................. C08F 222/40; C08F 271/02; C07C 207/00

(52) U.S. Cl. .................. 525/216; 525/218; 525/282; 526/262; 526/283; 526/284; 526/281; 526/308; 562/435

(58) Field of Search ................... 526/282, 283, 526/284, 281, 308, 309; 525/216, 218

(56) References Cited

FOREIGN PATENT DOCUMENTS

JP         04368358      *  4/1995

* cited by examiner

*Primary Examiner*—James J. Seidleck
*Assistant Examiner*—Olga Asinovsky
(74) *Attorney, Agent, or Firm*—Stephen E. Reiter; Foley & Lardner

(57) ABSTRACT

In accordance with the present invention, there are provided novel heterobifunctional monomers and uses for the same. Invention compounds have many of the properties required by the microelectronics industry, such as, for example, hydrophobicity, high $T_g$ values, low dielectric constant, ionic purity, low coefficient of thermal expansion (CTE), and the like. These properties result in a thermoset that is particularly well suited to high performance applications where typical operating temperatures are often significantly higher than those at which prior art materials were suitable. Invention compounds are particularly ideal for use in the manufacture of electronic components, such as, for example, printed circuit boards, and the like.

37 Claims, No Drawings

HETEROBIFUNCTIONAL MONOMERS AND USES THEREFOR

FIELD OF THE INVENTION

The present invention relates to novel heterobifunctional monomers useful in a variety of applications related to the preparation of components employed in the electronics industry. In a particular aspect, the present invention relates to formulations useful for the preparation of laminates. In another aspect, the present invention relates to formulations useful for the preparation of solder masks. In yet another aspect, the present invention relates to formulations useful for the preparation of liquid encapsulant for electronic components. In still another aspect, the present invention relates to formulations useful for the preparation of non-hermetic electronic packages.

BACKGROUND OF THE INVENTION

As the electronics industry advances, and production of light weight components increases, the development of new materials gives producers increased options for further improving the performance and ease of manufacture of such components. Materials used in the manufacture of electronic components include the resin required for the preparation of prepregs (which are, in turn, used for the preparation of multilayered printed circuit boards and printed wiring boards), resins used for the preparation of solder masks (which define solder areas on the multilayered printed wiring board), and resins used for preparation of glob top (which protects microelectronic devices from the environment).

Multilayered printed circuit boards are currently produced mainly by (a) a mass laminating technique and (b) a pin laminating technique. In these techniques, a printed circuit board for inner layer use (hereinafter, referred to as "inner-layer board") is first manufactured. This inner-layer board is combined with prepregs and then a copper foil or a single-side copper-clad laminate and the superimposed laminating materials are laminated to give a multilayered board, both sides of which are covered by a copper coating. This multilayered structure is processed as appropriate to form through-holes, outer-layer printed circuits, etc.

The initial manufacture of resins used in laminates is usually conducted by chemical producers and supplied to the trade in a workable form. Addition of a curing agent or catalyst, as well as optional components such as diluents, flow promoters, fire retardants, and other modifying resins is typically performed by the user. This may be done in the interest of customization to the application or to ensure that pre-reaction of the formulation does not occur.

Another common use of resins in the electronics industry is for the preparation of solder masks. Solder mask is used to prevent excessive flow of solder in plastic packages. The material used must maintain the integrity of the physical, chemical, mechanical, and environmentally related properties of the package. Solder masks were originally intended to be used on printed wiring boards (PWBs) as an aid to manufacturing, reducing the need for touch-up after machine soldering, reducing solder consumption, and providing mechanical protection for the main portion of the circuitry.

The main type of solder mask employed in the art is the "liquid photoimageable" solder mask. There are three primary methods of applying this type of soldermask: flood screen-coating, curtain, and spray coating. Each method has both advantages and drawbacks. Screen coating, for example, is efficient in material usage, but through-holes may be plugged in the process. These holes must then be vacated during development. Curtain coating is also efficient, but it is a much slower process since only one side of a board can be coated at a time. Spray coating is the best method to accomplish complete fill and trace application, but this technique can result in substantial material losses (e.g., in the range of 10–30% waste).

Another common use of resins in the electronics industry is as a liquid encapsulant (also referred to as "glob top"), wherein an aliquot of resin material is used to encase a component to protect it from certain stresses and from exposure to the environment. To meet the industry's ever-increasing demand for device reliability, materials for encapsulant applications must meet increasingly stringent performance requirements. Such requirements include excellent moisture resistance, ionic purity, low dielectric constant and good thermal properties. In the absence of these properties, especially in the presence of moisture and ionic impurities, corrosion (and ultimately failure of the device) will likely occur.

Yet another common use of resins in the electronics industry is in the preparation of non-hermetic electronic packages. Examples of such packages are ball grid array (BGA) assemblies, super ball grid arrays, IC memory cards, chip carriers, hybrid circuits, chip-on-board, multi-chip modules, pin grid arrays, and the like. In these structures, moisture resistance is an important consideration, both in terms of handling during assembly and reliability of the finished part. For example, absorption of moisture during assembly frequently leads to "popcorning" (the sometimes violent release of absorbed moisture upon heating to solder reflow temperatures). The development of moisture resistant resins for use in the preparation of non-hermetic electronic packages would be of great benefit to the art.

For all these applications, the microelectronics industry continues to require new resins which are able to meet its varying demands. Accordingly, there is a need for the development of materials to address the requirements of this rapidly evolving industry.

BRIEF DESCRIPTION OF THE INVENTION

In accordance with the present invention, there are provided novel heterobifunctional monomers and thermoset materials derived therefrom. Invention compounds have many of the properties required by the microelectronics industry, such as, for example, hydrophobicity, high $T_g$ values, low dielectric constant, ionic purity, low coefficient of thermal expansion (CTE), and the like. These properties result in a thermoset that is particularly well suited to high performance applications where typical operating temperatures are often significantly higher than those at which prior art materials were suitable. Invention compounds are particularly ideal for use in the manufacture of electronic components, such as, for example, printed circuit boards, and the like.

DETAILED DESCRIPTION OF THE INVENTION

In accordance with the present invention, there are provided heterobifunctional monomers having structure (I) as follows:

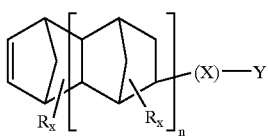

(I)

wherein:
  each R is independently hydrogen, lower alkyl, —Br, or —I,
  X is an optional bridging group,
  Y is maleimido, substituted maleimido, epoxy, cyanate ester-substituted aryl, propargyl-substituted aryl, ethynyl-substituted aryl, oxazoline, or benzoxazine,
  n ≦ about 8, and
  each x is independently 0, 1 or 2.

As will be readily recognized by those of skill in the art, the bridging group X may be any one of a number of suitable spacers, depending on the desired final properties of the monomer. X groups contemplated for use in the practice of the present invention include alkylenes or oxyalkylenes comprising up to about 20 carbon atoms, arylenes, siloxanes, and the like. Prefered bridging groups include alkylenes. Most preferred bridging groups include $C_1$–$C_6$ alkylenes.

Similarly, the Y groups indicated in structure (I) will vary according to the desired properties of the resulting monomers. Preferred functional groups defined by Y include maleimide, epoxy, cyanate ester-substituted aryl, oxazoline, and benzoxazine. Presently preferred Y groups are optionally substituted maleimido moieties. Substituents contemplated for use with maleimido Y groups include independently selected lower alkyls, halogens, and the like. Preferred substituents contemplated for use with maleimido Y groups include methyl and —Br.

Examples of heterobifunctional monomers embraced by structure (I) include those having structures II–VI as follows:

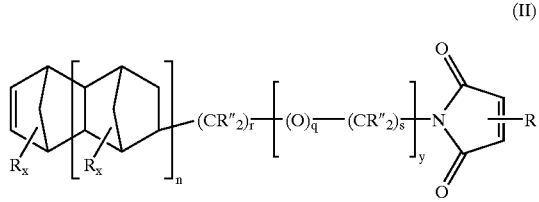

(II)

wherein:
  n, R and x are as defined above,
  R″ is hydrogen or lower alkyl,
  y is 0 up to 20,
  q is 0 or 1,
  r is 0 up to about 10, and
  s is 0 up to about 10;

wherein:
  n, R, R″, x, y, q, r, and s are as defined above;

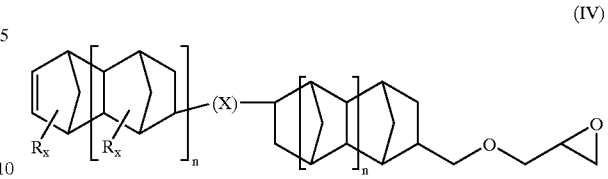

(IV)

wherein:
  X is an optional bridging group, and
  n, R, and x are as defined above;

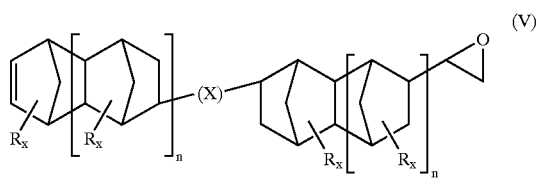

(V)

wherein:
  X is an optional bridging group, and
  n, R, and x are as defined above;

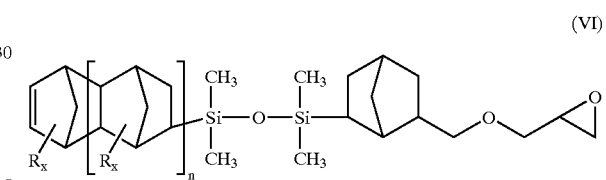

(VI)

wherein:
  n, R, and x are as defined above.

In another embodiment of the present invention, there are provided polymers of the above described heterobifunctional monomers. Because invention monomers are heterobifunctional, those of skill in the art will readily recognize that a wide variety of types of polymers can be generated by varying the reaction conditions, the nature of the pendant functional group Y, optional presence of comonomers, and the like. For example, the double bond functional group of the norbornyl moiety of invention monomers (hereinafter the "head") can be polymerized with the double bond functional group of other invention monomers (i.e., head-to-head polymers), the Y group functionalities (hereinafter the "tail") can be polymerized with one another (i.e., tail-to-tail polymers), the norbornyl functionalities can be polymerized with the Y group functionalities (i.e., head-to-tail polymers), and combinations thereof. For example, a polymer could be prepared with blocks of head-to-head, linked to blocks of tail-to-tail, blocks of head-to-tail, and the like.

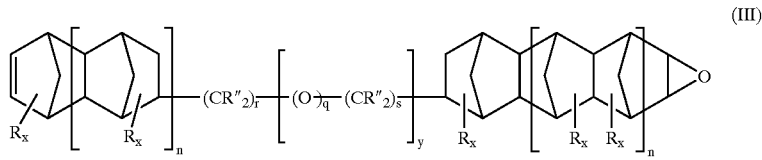

(III)

Of course, comonomers may be included in block co-polymers described above as well. For example, blocks of comonomers can be prepared and interspersed between blocks of invention monomers. Alternatively, comonomers may participate randomly in the preparation of polymers according to the present invention. In another embodiment, comonomers can alternate with invention monomers in a first orientation to form a first block, while interacting in a second orientation to form a second block, and so forth. Thus, a block copolymer comprising any possible combination of linkages between monomers and one or more comonomers is contemplated as falling within the scope of the present invention.

In a further embodiment of the present invention, there are provided polymers having the structure (VII) as follows:

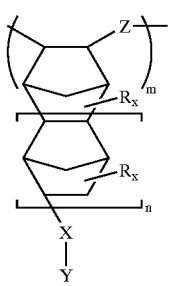

(VII)

wherein:
each R is independently hydrogen, lower alkyl, —Br, or —I,
X is an optional bridging group,
Y is a maleimido, a substituted maleimido, an epoxy group, a cyanate ester-substituted aryl, a propargyl or ethynyl substituted aryl, an oxazoline, or a benzoxazine,
each Z is optionally present, and when present, is independently derived from any cationically polymerizable monomer, any free-radically polymerizable monomer, or any coordinatively polymerizable monomer,
m is in the range of about 3 up to about 10,000,
n≦about 8, and
x is 0 up to 2.

Similarly, in another embodiment of the present invention, there are provided polymers having the structure (VIII) as follows:

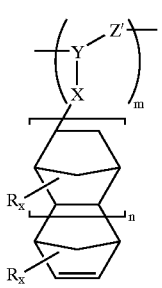

(VIII)

wherein:
R, X, Y, n, m, and x are as defined above,
each Z' is optionally present, and when present, is independently derived from any cationically polymerizable monomer, any anionically polymerizable monomer, any free-radically polymerizable monomer, or any coordinatively polymerizable monomer.

Cationically polymerizable monomers contemplated for use in the preparation of polymers having the structure (VIII) include styrenes, epoxies, vinyl ethers, benzoxazines, oxazolines, and the like.

Anionically polymerizable monomers contemplated for use in the preparation of polymers having the structure (VIII) include styrenes, maleimides, (meth)acrylates, and the like.

Free-radically polymerizable monomers contemplated for use in the preparation of polymers having the structure (VIII) include maleimides, (meth)acrylates, styrenes, vinyl esters, allyl ethers, allyl esters, and the like.

Coordinatively polymerizable monomers contemplated for use in the preparation of polymers having the structure (VIII) include $\alpha$-olefins, cyanates, ethynyls, propargyls, and the like.

In one embodiment of the present invention, X in structures (IV), (V), (VII), and (VIII) is an alkylene or oxyalkylene having up to about 20 carbon atoms, an arylene, or a siloxane.

Oxyalkylenes contemplated for use in the practice of the present invention have the structure:

$$-(CR''_2)_r-(O-)_q-(CR''_2)_s-$$

wherein:
each R'' is independently hydrogen, lower alkyl or aryl,
r falls in the range of 1 up to about 10,
s falls in the range of 1 up to about 10, and
q is 0 or 1.

Arylenes contemplated for use in the practice of the present invention include phenylene, naphthylene, and the like.

Siloxanes contemplated for use in the practice of the present invention include siloxanes having the structure:

$$-(CR_2)_{m'}-[Si(R')_2-O]_{q'}-Si(R')_2-(CR_2)_{n'}-$$

wherein:
each R is independently defined as above,
each R' is independently selected from hydrogen, lower alkyl or aryl,
m' falls in the range of 1 up to 10,
n' falls in the range of 1 up to 10, and
q' falls in the range of 1 up to 50.

In another embodiment of the present invention, there are provided thermosetting resin compositions comprising a base formulation comprising:
(a) a heterobifunctional monomer as described herein;
(b) in the range of about 0.2 up to about 5 wt % of at least one curing catalyst, based on the total weight of the composition;
(c) optionally, at least one polycyanate ester monomer; and
(d) optionally, at least one polycyclic olefin having at least one terminal norbornene functional group.

Cyanate esters contemplated for use in the practice of the present invention include those described in U.S. Pat. No. 5,789,757, the entire contents of which are incorporated by reference herein.

As readily recognized by those of skill in the art, a wide variety of curing catalysts can be employed in the preparation of invention compositions. The preferred catalyst to be used will, of course, depend on the monomer vehicle(s) employed. For example, for those monomer vehicles which cure by a free radical mechanism, free radical initiators such as peroxy esters, peroxy carbonates, hydroperoxides, alkylperoxides, arylperoxides, azo compounds, and the like can be employed.

For those monomer vehicles which cure by cationic and/or anionic polymerization, organic bases, cationic catalysts, transition metal catalysts, and the like can be employed. Exemplary organic bases contemplated for use herein include tertiary amines (e.g., N,N-dimethyl aniline, N,N-dimethyl toluidine, N,N-dimethyl-p-anisidine, p-halogeno-N,N-dimethyl anilines, 2-N-ethyl aniline ethanol, tri-n-butyl amine, pyridine, quinoline, N-methyl morpholine, triethanolamine, and the like); imidazoles (e.g., imidazole or benzimidazole); phenols (e.g., phenol, cresol, xylenol, resorcinol, phloroglucin, and the like), and the like.

Exemplary cationic catalysts contemplated for use herein include onium salts, iodonium salts, sulfonium salts, and the like.

Exemplary metal catalysts contemplated for use herein include titanium, zirconium, hafnium, lead, zinc, tin, manganese, nickel, copper, cobalt and the like, in the form of a chelate, a soap, or the like. Examples of such compounds include metallocenes of titanium, zirconium, or haffnium, lead naphthenate, lead stearate, zinc naphthenate, tin oleate, dibutyl tin maleate, manganese naphthenate, cobalt naphthenate, lead salt of resin acid, chlorides such as $ZnCl_2$, $SnCl_4$ or $AlCl_3$, and the like.

Polycyclic olefins contemplated for optional use in thermosetting resins of the present invention include maleimides, substituted maleimides, epoxies, oxazolines, oxazines, cyanate ester-substituted aryls, and the like. Exemplary polycyclic olefins include those having structures (IX) and (X) as follows:

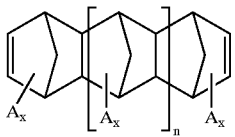

(IX)

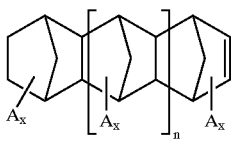

(X)

wherein:
each A is
(a) independently an alkyl or substituted alkyl and each x is independently 0, 1 or 2, or
(b) -X'-Y',
wherein:
X' is an optional bridging group
Y' is maleimido, substituted maleimido, epoxy, oxazoline, cyanate ester-substituted aryl, or a benzoxazine, and
n ≦ about 8.

Optional bridging groups X' contemplated for use in structures (IX) and (X) include (oxy)alkylenes (i.e., alkylenes or oxyalkylenes) comprising up to about 20 carbon atoms.

Optionally, invention compositions can further contain one or more of the following additional components: anti-oxidants, bleed control agents, one or more fillers, inert (i.e., nonreactive) diluents, reactive diluents, coupling agents, adhesion promoters, flexibilizers, dyes, pigments, and the like.

Anti-oxidants contemplated for use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis(α,α-dimethylbenzyl) diphenylamine, and the like), phosphites, and the like. When used, the quantity of anti-oxidant typically falls in the range of about 100 up to 2000 ppm, relative to the weight of the base formulation.

Bleed control agents contemplated for use in the practice of the present invention include cationic surfactants, tertiary amines, tertiary phosphines, amphoteric surfactants, polyfunctional compounds, and the like, as well as mixtures of any two or more thereof. Those of skill in the art recognize that the quantity of bleed control agent employed in the practice of the present invention can vary widely, typically falling in the range of about 0.1 up to about 10 wt %, relative to the weight of the base formulation.

Fillers traditionally employed for the preparation of resin materials having electrically insulating properties are non-conductive materials such as, for example, aluminum nitride, boron nitride, alumina, silicon dioxide, teflon, polyolefins, and the like. Those of skill in the art readily recognize that the desirability of including filler in the invention composition will depend on the end use contemplated therefor. Thus, for example, when preparing compositions for use as a solder mask, filler is not typically employed. Conversely, when preparing compositions for use as a liquid encapsulant, it is desirable to include substantial quantities of filler therein (typically in the range of about 10 up to 75 wt % filler, relative to the weight of the base formulation).

While the use of inert diluents is not excluded from the practice of the present invention, it is generally preferred that compositions according to the invention remain substantially free of solvent, so as to avoid the potentially detrimental effects thereof, e.g., creation of voids caused by solvent escape, the environmental impact of vaporized solvent, the redeposition of outgassed molecules in the surface of the article, and the like. When used, suitable inert diluents include dimethylformamide, dimethylacetamide, N-methylpyrrolidone, toluene, xylene, methylene chloride, tetrahydrofuran, glycol ethers, methyl ethyl ketone or monoalkyl or dialkyl ethers of ethylene glycol, polyethylene glycol, propylene glycol, polypropylene glycol, and the like. When used, inert diluents are typically present in the range of about 10 up to 40 wt %, relative to the weight of the base formulation.

Reactive diluents contemplated for use in the practice of the present invention include any reactive diluent which, in combination with the maleimide-based formulations described herein, forms a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like. When used, reactive diluents are typically present in the range of about 5 up to 15 wt %, relative to the weight of the base formulation.

In a particular aspect, compositions according to the invention optionally further contain in the range of about 0.1 up to about 10 wt % of at least one coupling agent, based on the total weight of the composition. Coupling agents contemplated for use in the practice of the present invention include silicate esters, metal acrylate salts, titanates or compounds containing a co-polymerizable group and a chelating ligand.

Adhesion promoters contemplated for use in the practice of the present invention include polymers that have pendant acid or latent acid groups that can increase adhesion. An example is the Ricon R-130 20% maleated (Ricon Resins, Inc., Grand Junction, Colo.), a polybutadiene with anhydride groups that can react with a surface to increase adhesion. When present, adhesion promoters are typically present in the range of about 5 up to 30 wt %, relative to the weight of the base formulation.

Flexibilizers contemplated for use in the practice of the present invention include branched polyalkanes or polysiloxanes that lower the $T_g$ of the formulation. An example of such a material would be polybutadienes such as the Ricon R-130 as described hereinabove. When present, flexibilizers are typically present in the range of about 15 up to about 60 wt %, relative to the weight of the base formulation.

Dyes contemplated for use in the practice of the present invention include nigrosine, Orasol blue GN, phthalocyanines, and the like. When used, organic dyes in relatively low amounts (i.e., amounts less than about 0.2 wt %) provide contrast.

Pigments contemplated for use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 wt %, relative to the weight of the base formulation.

As readily recognized by those of skill in the art, the quantity of the various components employed to prepare invention compositions can vary within wide ranges. For example, the quantity of the heterobifunctional monomer component typically falls in the range of about 10 up to 99.8 wt % of the base formulation, the quantity of polycyanate ester monomer(s) typically comprise(s) in the range of about 0 up to 89.8 wt % of the base formulation, the quantity of polycyclic olefin having at least one terminal norbornene functional group typically comprises in the range of about 0 up to 89.8 wt % of the base formulation, and the curing catalyst typically comprises in the range of about 0.2 up to about 5 wt % of the base formulation, wherein wt % in all instances is based on the total weight of all components of the base formulation.

In accordance with additional embodiments of the present invention, there are provided methods for the synthesis of the various monomers described herein. Thus, in one embodiment of the present invention, there is provided a method for synthesizing heterobifunctional monomers of structure (I), said method comprising contacting a primary amine with an optionally substituted maleic anhydride, or an epoxy, under cyclodehydration reaction conditions, wherein said primary amine has the structure:

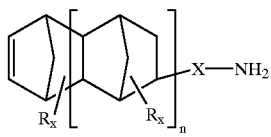

and wherein R, X, x, and n are as defined above

In another embodiment of the present invention there is provided a method for synthesizing a polymer comprising a plurality of heterobifunctional monomers of structure (I), said method comprising subjecting a plurality of said heterobifunctional monomers to a Zeigler-type coordinative reaction, a cationic cure, an anionic cure, a free radical ring opening or a ring-opening metathesis reaction.

In another aspect of the foregoing embodiment, there is provided a method for synthesizing a polymer of invention heterobifunctional monomers of structure (I), wherein the norbornyl functional groups of said heterobifunctional monomers are polymerized, said method comprising subjecting a plurality of said heterobifunctional monomers to a Zeigler-type coordinative reaction, a cationic cure, or a free radical ring opening.

In another aspect of the foregoing embodiment, there is provided a method for synthesizing a polymer of invention heterobifunctional monomers of structure (I), wherein the Y functional groups of said heterobifunctional monomers are polymerized, said method comprising subjecting a plurality of said heterobifunctional monomers to an anionic cure.

In another aspect of the foregoing embodiment, there is provided a method for synthesizing a polymer of invention heterobifunctional monomers of structure (I), wherein alternating norbornyl functional groups of said heterobifunctional monomers are polymerized with the Y functional groups of said heterobifunctional monomers, said method comprising subjecting a plurality of said heterobifunctional monomers to a free radical cure.

In another embodiment of the present invention there is provided a method for synthesizing a block copolymer comprising:

(a) one or more blocks of a plurality of polymerized heterobifunctional monomers as described herein, (b) one or more blocks of a polymerized comonomer selected from the group consisting of said heterobifunctional monomer, an optionally substituted maleimido, an epoxy group, an oxazoline, a cyanate ester-substituted aryl, and an oxazine, wherein the block(s) of (a) are different from the block(s) of (b); said method comprising (a) synthesizing a first block polymer by subjecting a first plurality of said heterobifunctional monomers to a Zeigler-type coordinative reaction, a cationic cure, or a free radical ring opening, (b) synthesizing a second block polymer by subjecting a second plurality of heterobifunctional monomers to a free radical reaction, an anionic cure, or a UV catalyzed cationic cure, and (c) subjecting a plurality of first and second block polymers to one or more of a Zeigler-type coordinative reaction, a cationic cure, an anionic cure or a ring-opening metathesis reaction.

In still another embodiment of the present invention, there is provided a method for synthesizing a polymer having structure (VII), said method comprising subjecting a plurality of monomers comprising any cationically polymerizable monomer, any free-radically polymerizable monomer, or any coordinatively polymerizable monomer, and monomers of structure (I) to one or more of a Zeigler-type coordinative reaction, a cationic cure, an anionic cure, a free radical ring opening or a ring-opening metathesis reaction.

In yet another embodiment of the present invention, there is provided a method for synthesizing a polymer having structure (VIII), said method comprising subjecting a plurality of monomers comprising any cationically polymerizable monomer, any free-radically polymerizable monomer, or any coordinatively polymerizable monomer, and monomers of structure (I) to one or more of a Zeigler-type coordinative reaction, a cationic cure, an anionic cure, a free radical ring opening or a ring-opening metathesis reaction.

In accordance with another embodiment of the present invention, there are provided assemblies comprising a first article permanently adhered to a second article by the adhesive properties of the base formulation described herein. Examples of the types of articles contemplated for preparation in accordance with the present invention include laminated circuit boards (i.e., the first article and the second article are separate layers of a laminate structure), printed wiring boards, and the like.

Examples of the base materials contemplated for use in the preparation of laminates include woven fabrics of various glasses such as E-glass, S-glass, SII-glass, D-glass, quartz glass, and the like, and other inorganic woven fabrics such as alumina paper; woven fabrics made of super heat-resistant resins such as all-aromatic polyamides, polyimides, fluoroplastics, poly(phenylene sulfide), polyetheretherketones, polyetherimides, liquid-crystal polyester resins, and the like; woven fabrics obtained using composite yarns comprising combinations of fibers of the above inorganic materials and fibers of the above super heat-resistant resins; and other woven fabrics including those comprising suitable combinations of the above.

Thus, when formulations as described herein are used for the preparation of laminates, the quantity of the heterobifunctional monomer component typically falls in the range of about 15 up to about 30 wt % of the base formulation, while the quantity of polycyanate ester monomer(s) typically comprise(s) in the range of about 65 up to about 84.8 wt % of the base formulation, and the curing catalyst typically comprises in the range of about 0.2 up to about 5 wt % of the base formulation, wherein wt % in all instances is based on the total weight of all components of the base formulation.

In accordance with yet another embodiment of the present invention, there are provided articles comprising a circuit board having a solder mask deposited thereon, wherein said solder mask is prepared from compositions described herein. Solder masks are widely used in the electronics industry, and are well known to those of skill in the art. Thus, those of skill in the art can readily determine how to use the compositions described herein for such applications.

Thus, when formulations as described herein are used for the preparation of solder mask, the quantity of the maleimide component typically falls in the range of about 95 up to about 99.8 wt % of the base formulation, while polycyanate ester monomer(s) is typically not added. Curing catalyst typically falls in the range of about 0.2 up to about 5 wt % of the base formulation, wherein wt % in all instances is based on the total weight of all components of the base formulation.

In accordance with yet another embodiment of the present invention, there are provided articles comprising an electronic component encased within an aliquot of the above-described thermosetting composition. For this specific application of invention compositions, it is desirable to include filler therein in order to enhance the rheological properties thereof.

Thus, when formulations described herein are used for the preparation of a glob top, the quantity of the heterobifunctional monomer component typically falls in the range of about 15 up to about 40 wt % of the base formulation, while the quantity of polycyanate ester monomer(s) typically comprise(s) in the range of about 55 up to about 84.8 wt % of the base formulation, and the curing catalyst typically comprises in the range of about 0.2 up to about 5 wt % of the base formulation, wherein wt % in all instances is based on the total weight of all components of the base formulation.

Alternatively, when formulations described herein are used for the preparation of a glob top, a formulation based predominantly on maleimide-based heterobifunctional monomers can be employed, i.e., the quantity of the maleimide-based monomer component typically falls in the range of about 95 up to about 99 wt % of the base formulation, and the curing catalyst typically falls in the range of about 1 up to about 5 wt % of the base formulation, wherein wt. percent in all instances is based on the total weight of all components of the base formulation.

In accordance with another embodiment of the present invention, there are provided improved non-hermetic electronic packages, wherein the improvement comprises employing a maleimide-based composition as described herein for each component of the package, i.e., wherein heterobifunctional monomers according to the invention are employed for the preparation of the maleimido-based composition.

Those of skill in the art recognize that many different electronic packages would benefit from preparation using the hydrophobic maleimide-based resins described herein. Examples of such packages include ball grid arrays, super ball grid arrays, IC memory cards, chip carriers, hybrid circuits, chip-on-board, multi-chip modules, pin grid arrays, chip size packages (CSPs), and the like.

The invention will now be described in greater detail by reference to the following non-limiting examples.

EXAMPLE 1

This example describes the synthesis of the heterobifunctional monomer, N-(5-norborn-2-en-yl) maleimide, shown below:

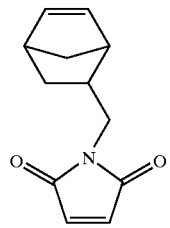

A. Preparation of 5-methylamino-norbornene. Allylamine (113 g, 1.98 mol) and dicyclopentadiene (DCPD) (65 g, 0.49 mol) were placed into an autoclave and heated to 220° C. for 24 hours. Excess allylamine was removed by distillation at atmospheric pressure. The 1:1 cyclopentadiene:allylamine Diels-Alder adduct was purified by vacuum distillation (55 g collected at 55–65° C. at 1 mm Hg). $^1$H and $^{13}$C NMR data were consistent with that expected for the 1:1 Diels-Alder adduct of cyclopentadiene and allylamine (see Sagane, *Makromol. Chemie*, 1993, 194, 37). Infrared spectroscopy confirmed the presence of the amino functional group.

B. Preparation of N-(5-norborn-2-en-yl) maleimide. Maleic anhydride (14.7 g, 0.150 mol) was dissolved in toluene (100 ml) in a two-neck round bottom flask. To this solution was slowly added $CH_3SO_3H$ (5.8 ml, 0.090 mol) followed by $NEt_3$ (12 mL, 0.087 mol). 5-methylamino-norbornene (17 g, 0.14 mol) was dissolved in toluene (15 ml) and added dropwise to the maleic anhydride solution over a 1 hour period. After amine addition was complete, the flask was equipped with a reflux condenser and a Dean-Stark trap and allowed to reflux for 16 hours. The toluene solution was washed with water, dried with MgSO$_4$, and the toluene was removed in vacuo to afford 20 g of a yellow solid. Infrared spectroscopy confirmed the presence of the maleimide group (1706 cm$^{-1}$, 825 cm$^{-1}$, 694 cm$^{-1}$) and $^1$H and $^{13}$C NMR spectroscopy were consistent with the formation of N-(5-norborn-2-en-yl) maleimide.

EXAMPLE 2

Copolymerization of Norbornene and N-(5-Norborn-2-en-yl)maleimide

N-(5-norborn-2-en-yl) maleimide (1.0 g, 4.9 mmol) and norbornene were weighed into a 100 ml septum-capped vial equipped with a stir bar. The vial was purged with argon for 15 min and the vial was re-weighed to determine the actual amount of norbornene remaining in the vial, i.e., 0.78 g, 8.3 mmol (norbornene is volatile, therefore some of this monomer was lost during the argon purge). To the vial was added chlorobenzene (2 mL, chlorobenzene was dried over CaH$_2$ prior to use). The catalyst system, i.e., (allyl)PdCl (39 mg, 0.11 mmol) and AgSbF$_6$ (98 mg, 0.29 mmol) (see Risse, et. al., *Macromolecules*, 1996, 29, 2755) was weighed into a separate septum-capped vial and inmmediately purged with argon. After a 15 min purge, chlorobenzene (2 mL) was added to the catalyst mixture, and this mixture was allowed to stir at room temperature for 30 minutes. The catalyst solution was injected into the monomer solution using a syringe equipped with a 45 μm filter to remove the precipitated AgCl. The copolymerization mixture was allowed to stir at room temperature for 20 hrs. At this time, the viscosity of the solution had increased considerably. The solution was diluted with chlorobenzene (15 mL) and poured into a large excess of methanol (150 mL) to precipitate the copolymer and wash away any unreacted monomer and catalyst residues. The copolymer was isolated by filtration and dried in vacuo overnight at 70° C. to afford 700 mg (40% yield) of a white solid. Infrared spectroscopy confirmed the presence of the unreacted maleimide group, indicating polymerization had proceeded through the norbornene double bond only. $^1$H NMR spectroscopy further confirms the incorporation of the maleimide group into the copolymer (CDCl$_3$, δ 6.7, 2H, maleimido protons). Additionally, a differential scanning calorimetry analysis (DSC) was performed on the polymer revealing a large exotherm (peak at 323° C.), consistent with thermal crosslinking of the maleimide group.

EXAMPLE 3

Copolymerization of 5-n-Butyl-norbornene and N-(5-Norborn-2-en-yl)maleimide

N-(5-norborn-2-en-yl) maleimide (44 g, 0.20 mol) and 5-n-butyl-norbornene (44 g, 0.30 mol) were weighed into a two-neck round bottom flask and immediately placed under an atmosphere of argon. Via cannula, 1-Hexene (124 mL, 1.0 mol) was added as a chain transfer agent, followed by the reaction solvent CH$_2$Cl$_2$ (300 mL, dried over CaH$_2$ prior to use). The catalyst system, (allyl)PdCl (0.90 g, 2.5 mmol) and AgSbF$_6$ (2.3 g, 6.8 mmol) was prepared and introduced to the polymerization flask as described in Example 2. The polymerization was allowed to proceed for 48 hrs.

The polymerization solution was poured into a large excess of acetone (1 L) to precipitate the polymer and remove unreacted monomer and catalyst residues. The polymer was isolated by filtration and dried in vacuo at room temperature overnight. In this manner 48 g (55% yield) of a white solid was obtained. Infrared spectroscopy and $^1$H and $^{13}$C NMR spectroscopy confirmed the presence of the unreacted maleimide functional group, indicating polymerization had proceeded through the norbornenyl double bond only.

While the invention has been described in detail with reference to certain preferred embodiments thereof, it will be understood that modifications and variations are within the spirit and scope of that which is described and claimed.

What is claimed is:

1. A heterobifunctional monomer of the following structure:

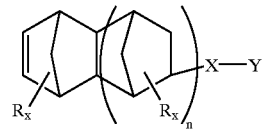

wherein:

each R is independently hydrogen, lower alkyl, —Br, or —I,

X is a covalent bond or a bridging group containing more than one carbon atom,

Y is maleimido, substituted maleimido, epoxy, oxazoline, cyanate ester-substituted aryl, propargyl-substituted aryl, ethynyl-substituted aryl, or benzoxazine, n≦about 8, and each x is independently 0, 1, or 2.

2. The heterobifunctional monomer according to claim 1, wherein X is alkylene or oxy-alkylene comprising from 2 up to about 20 carbon atoms, arylene, or siloxane.

3. The heterobifunctional monomer according to claim 2, wherein X is alkylene comprising from 2 up to about 20 carbon atoms.

4. The heterobifunctional monomer according to claim 3, wherein said alkylene is C$_2$ to C$_6$ alkylene.

5. The heterobifunctional monomer according to claim 1, wherein Y is an optionally substituted maleimido.

6. The heterobifunctional monomer according to claim 5, wherein said maleimido is substituted with 1 or 2 independently selected lower alkyls, —Br, or —I.

7. A heterobifunctional monomer of the following structure:

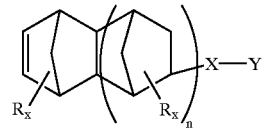

wherein:

each R is independently hydrogen, lower alkyl, —Br, or —I,

X is an optional bridging group,

Y is an epoxy, oxazoline, cyanate ester-substituted aryl, propargyl-substituted aryl, ethynyl-substituted aryl, or benzoxazine, n≦about 8, and each x is independently 0, 1, or 2.

8. A heterobifunctional monomer of the following structure:

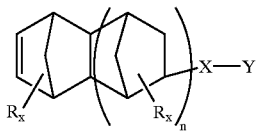

wherein:
  each R is independently hydrogen, lower alky, —Br, or —I,
  X is an optional bridging group,
  Y is maleimido, substituted maleimido, epoxy, oxazoline, cyanate ester-substituted aryl, propargyl-substituted aryl, ethynyl-substituted aryl, or benzoxazine,
  n is 0 or greater than 1 up to about 8, and
  each x is independently 0, 1, or 2.

9. A polymer comprising a plurality of heterobifunctional monomers according to claim 1.

10. The polymer according to claim 9, wherein said norbornyl functional groups of said heterobifunctional monomers are polymerized.

11. The polymer according to claim 9, wherein said Y functional groups of said heterobifunctional monomers are polymerized.

12. The polymer according to claim 9, wherein alternating norbornyl functional groups of said heterobifunctional monomers are polymerized with the Y functional groups of said heterobifunctional monomers.

13. A block copolymer comprising:
  (a) one or more blocks of a plurality of polymerized heterobifunctional monomers according to claim 1;
  (b) one or more blocks of a polymerized comonomer selected from the group consisting of said heterobifunctional monomer, an optionally substituted maleimido, an epoxy group, an oxazoline, a cyanate ester-substituted aryl, and a benzoxazine,
    wherein the block(s) of (a) are different from the block(s) of (b).

14. A polymer having the structure:

(VII)

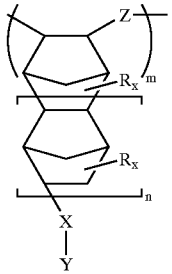

wherein:
  each R is independently hydrogen, lower alkyl, —Br, or —I,
  X is an optional bridging group,
  Y is a maleimido, substituted maleimido, epoxy, oxazoline, cyanate ester-substituted aryl, propargyl-substituted aryl, ethynyl-substituted aryl, or a benzoxazine
  each Z is optionally present, and when present, is independently derived from any cationically polymerizable monomer, any free-radically polymerizable monomer, or any coordinatively polymerizable monomer,
  m is in the range of about 3 up to about 10,000,
  n ≦ about 8, and
  x is 0 up to 2.

15. A polymer according to claim 14, wherein X is alkylene or oxy-alkylene comprising up to about 20 carbon atoms, arylene, or siloxane.

16. A polymer having the structure:

(VIII)

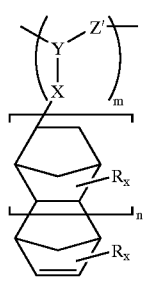

wherein:
  each R is independently hydrogen, lower alkyl, —Br, or —I,
  X is an optional bridging group,
  Y is maleimido, substituted maleimido, epoxy, oxazoline, cyanate ester-substituted aryl, propargyl-substituted aryl, ethynyl-substituted aryl, or a benzoxazine,
  each Z' is optionally present, and when present, is independently derived from any cationically polymerizable monomer, any anionically polymerizable monomer, any free-radically polymerizable monomer, or any coordinatively polymerizable monomer,
  m is in the range of about 3 up to about 10,000,
  n ≦ about 8, and
  x is 0 up to 2.

17. A polymer according to claim 16, wherein X is an alkylene or oxy-alkylene comprising up to about 20 carbon atoms, an arylene, or a siloxane.

18. A method for synthesizing heterobifunctional monomers according to claim 1, said method comprising contacting a primary amine with an optionally substituted maleic anhydride, or an epoxy, under cyclodehydration reaction conditions, thereby producing the desired heterobifunctional monomer, wherein said primary amine has the following structure:

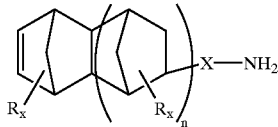

wherein:
  each R is independently hydrogen, lower alkyl, —Br, or —I,
  X is a covalent bond or a bridging group containing more than one carbon atom,
  Y is maleimido, substituted maleimido, epoxy, oxazoline, cyanate ester-substituted aryl, propargyl-substituted aryl, ethynyl-substituted aryl, or benzoxazine,
  n ≦ about 8, and
  each x is independently 0, 1, or 2.

19. A method for synthesizing a polymer according to claim 9, said method comprising subjecting a plurality of said heterobifunctional monomers to a Zeigler-type coordinative reaction, a cationic cure, an anionic cure, a free radical ring opening or a ring-opening metathesis reaction.

20. A method for synthesizing a polymer according to claim 10, said method comprising subjecting a plurality of said heterobifunctional monomers to a Zeigler-type coordinative reaction, a cationic cure, or a free radical ring opening.

21. A method for synthesizing a polymer according to claim 11, said method comprising subjecting a plurality of said heterobifunctional monomers to an anionic cure.

22. A method for synthesizing a polymer according to claim 12, said method comprising subjecting a plurality of said heterobifunctional monomers to a free radical cure.

23. A method for synthesizing a polymer according to claim 13, said method comprising
  (a) synthesizing a first block polymer by subjecting a first plurality of said heterobifunctional monomers to a Zeigler-type coordinative reaction, a cationic cure, or a free radical ring opening,
  (b) synthesizing a second block polymer by subjecting a second plurality of heterobifunctional monomers to a free radical reaction, an anionic cure, or a UV catalyzed cationic cure, and
  (c) subjecting a plurality of first and second block polymers to one or more of a Zeigler-type coordinative reaction, a cationic cure, an anionic cure or a ring-opening metathesis reaction.

24. A method for synthesizing a polymer according to claim 14, said method comprising subjecting to one or more of a Zeigler-type coordinative reaction, a cationic cure, an anionic cure, a free radical ring opening or a ring-opening metathesis reaction, a plurality of monomers Z and monomers of the following structure:

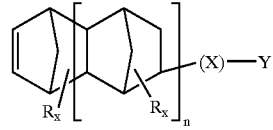

(I)

wherein:
  each R is independently hydrogen, lower alkyl, —Br, or —I,
  X is an optional bridging group,
  Y is maleimido, substituted maleimido, epoxy, oxazoline, cyanate ester-substituted aryl, ethynyl-substituted aryl, propargyl-substituted aryl, or benzoxazine,
  Z is optionally present, and when present, is independently any cationically polymerizable monomer, any anionically polymerizable monomer, any free-radically polymerizable monomer, or any coordinatively polymerizable monomer,
  $n \leq$ about 8, and
  each x is independently 0, 1 or 2.

25. A method for synthesizing a polymer according to claim 16, said method, comprising subjecting to one or more of a Zeigler-type coordinative reaction, a cationic cure, an anionic cure, a free radical ring opening or a ring-opening metathesis reaction, a plurality of monomers Z' and monomers of the following structure:

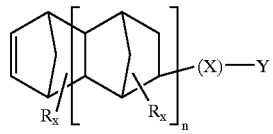

wherein:
  each R is independently hydrogen, lower alkyl, —Br, or —I,
  X is an optional bridging group,
  Y is maleimido, substituted maleimido, epoxy, oxazoline, cyanate ester-substituted aryl, ethynyl-substituted aryl, propargyl-substituted aryl or benzoxazine,
  Z' is optionally present, and when present, is independently any cationically polymerizable monomer, any anionically polymerizable monomer, any free-radically polymerizable monomer, or any coordinatively polymerizable monomer,
  $n \leq$ about 8, and
  each x is independently 0, 1 or 2.

26. A thermoset resin comprising a polymer according to claim 9.

27. A thermoset resin comprising a polymer according to claim 10.

28. A thermoset resin comprising a polymer according to claim 11.

29. A thermoset resin comprising a polymer according to claim 12.

30. A thermoset resin comprising a polymer according to claim 13.

31. A thermoset resin comprising a polymer according to claim 11.

32. A thermoset resin comprising a polymer according to claim 16.

33. A thermosetting resin composition comprising:
  (a) a heterobifunctional monomer according to claim 1,
  (b) in the range of 0.2 up to 5 wt % of at least one curing catalyst, based on the total weight of the composition
  (c) optionally, at least one hydrophobic cyanate ester monomer, and
  (d) optionally, at least one polycyclic olefin having at least one terminal norbornene functional group.

34. An assembly comprising a first article permanently adhered to a second article by a cured aliquot of the thermosetting resin composition according to claim 33.

35. An assembly according to claim 34, wherein said first article and said second article are separate layers of a laminated circuit board.

36. An article comprising a circuit board having a solder mask deposited thereon, wherein said solder mask is prepared from the composition according to claim 33.

37. An article comprising an electronic component encased within an aliquot of composition according to claim 33.

* * * * *

UNITED STATES PATENT AND TRADEMARK OFFICE
CERTIFICATE OF CORRECTION

PATENT NO.    : 6,423,780 B1
DATED         : July 23, 2002
INVENTOR(S)   : Stephen M. Dershem and Kevin J. Forrestal It is certified that error appears in the above-identified patent and that said Letters Patent is hereby corrected as shown below:

<u>Column 7,</u>
Line 57, change "haffnium" to -- hafnium --

<u>Column 15,</u>
Line 37, change "alky" to -- alkyl --

<u>Column 18,</u>
Line 64, change "11" to -- 14 --.

Signed and Sealed this

Twenty-first Day of January, 2003

JAMES E. ROGAN
*Director of the United States Patent and Trademark Office*